United States Patent [19]

Rose

[11] Patent Number: 4,602,030

[45] Date of Patent: Jul. 22, 1986

[54] FUNGICIDAL 2-SUBSTITUTED-1-(1-IMIDAZOLYL)-PROPYL ARYL SULFIDES, SULFOXIDES AND SULFONES

[75] Inventor: Allan F. Rose, Richmond, Calif.

[73] Assignee: Chevron Research Company, San Francisco, Calif.

[21] Appl. No.: 614,937

[22] Filed: May 24, 1984

[51] Int. Cl.[4] .................. A01N 43/50; C07D 233/60
[52] U.S. Cl. ..................................... 514/399; 548/341
[58] Field of Search .................. 548/341; 424/273 R; 514/399

[56] References Cited

U.S. PATENT DOCUMENTS

| | | | |
|---|---|---|---|
| 4,036,970 | 7/1977 | Walker et al. | 424/273 R |
| 4,203,995 | 5/1980 | Funaki et al. | 548/262 |
| 4,360,528 | 11/1982 | Jager et al. | 548/262 |
| 4,380,628 | 4/1983 | Elbe | 548/262 |
| 4,416,682 | 11/1983 | Worthington | 548/262 |
| 4,483,865 | 11/1984 | Meeres et al. | 548/341 X |

FOREIGN PATENT DOCUMENTS

| | | | |
|---|---|---|---|
| 52424 | 5/1982 | European Pat. Off. | 548/262 |
| 55833 | 7/1982 | European Pat. Off. | 424/273 R |
| 2908378 | 9/1980 | Fed. Rep. of Germany | 548/262 |

*Primary Examiner*—Richard A. Schwartz
*Assistant Examiner*—Kurt G. Briscoe

*Attorney, Agent, or Firm*—S. R. LaPaglia; T. G. DeJonghe; S. L. Biggs

[57] ABSTRACT

Compounds of the formula:

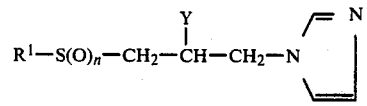

wherein n is 0, 1 or 2; $R^1$ is phenyl optionally substituted with 1 to 5 substitutents independently selected from halogen, lower alkyl, lower alkoxy, nitro, cyano, lower carbalkoxy or amino optionally substituted with 1 or 2 lower alkyl groups; and Y is hydroxy; halogen; $-OCH_2R^2$ wherein $R^2$ is lower alkyl, or lower alkenyl optionally substituted with 1 to 5 halogen atoms, or phenyl optionally substituted with 1 to 5 substituents independently selected from halogen, lower alkyl, nitro, lower alkoxy, cyano or lower carbalkoxy;

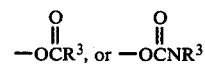

wherein $R^3$ is phenyl optionally substituted with 1 to 5 substituents independently selected from halogen, lower alkoxy, or nitro, are active as fungicides.

17 Claims, No Drawings

FUNGICIDAL 2-SUBSTITUTED-1-(1-IMIDAZOLYL)-PROPYL ARYL SULFIDES, SULFOXIDES AND SULFONES

BACKGROUND OF THE INVENTION

The present invention relates to 2-substituted-1-(1-imidazolyl)propyl aryl sulfides, sulfoxides and sulfones which have fungicidal activity.

In a world which has an ever-increasing population which is dependent for food on an ever-decreasing amount of arable land, it is important to develop agents which may help increase crop yields. For example, fungicides may increase crop production by protecting crops from destruction by fungi, including plant fungal diseases.

German Offenlegungsschrift No. 29 08 378 discloses 1,2,4-Triazolyl-2-propanol derivatives which are active as fungicides.

SUMMARY OF THE INVENTION

The present invention relates to 2-substituted-1-(1-imidazolyl)propyl aryl sulfides sulfoxides and sulfones of the formula:

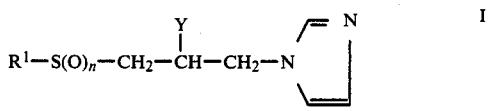

wherein n is 0, 1 or 2; $R^1$ is phenyl optionally substituted with 1 to 5 substituents independently selected from halogen, lower alkyl, lower alkoxy, nitro, cyano, lower carbalkoxy, or amino optionally substituted with 1 or 2 lower alkyl groups; and Y is hydroxy; halogen; $—OCH_2R^2$ wherein $R^2$ is lower alkyl or lower alkenyl optionally substituted with 1 to 3 halogen atoms, or phenyl optionally substituted with 1 to 5 substituents independently selected from halogen, lower alkyl, nitro, lower alkoxy, cyano or lower carbalkoxy;

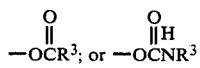

wherein $R^3$ is phenyl optionally substituted with 1 to 5 substituents independently selected from halogen, lower alkoxy or nitro; which are fungicidal.

Among other factors, the present invention is based upon my finding that the compounds of this invention are surprisingly effective in controlling fungi, especially fungi which may cause plant fungal diseases.

DETAILED DESCRIPTION OF THE INVENTION

The compounds of the present invention may be conveniently prepared according to the following reaction scheme:

(a) where n is 0 and Y is —OH

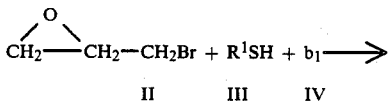

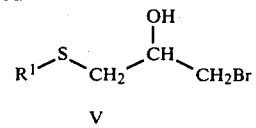

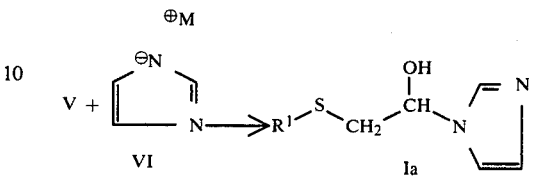

wherein $R^1$ is as defined in conjunction with formula (I), $b_1$, is a base and M is a metal cation.

Reaction (1) is conducted by combining approximately equimolar amounts of II and III in the presence of base $b_1$ and solvent. Although the reactants may be added in any order, it is preferred to add III to a mixture of II, and IV in solvent. The reaction is conducted at a temperature of about $-20°$ C. to about 100° C., and is generally complete within about 1 to about 10 hours. Suitable solvents include water, methanol, ethanol, tetrahydrofuran or mixtures thereof. Suitable bases, $b_1$, include organic bases such as triethylamine; and inorganic bases such as sodium hydroxide, sodium bicarbonate, sodium carbonate, potassium hydroxide, potassium bicarbonate, potassium carbonate and the like. The product V is isolated by conventional procedures such as concentration, extraction, filtration, washing, chromatography, distillation and the like.

Reaction (2) is conducted by combining approximately equimolar amounts V and VI in solvent. Although the reactants may be combined in any order, it is preferred to add V in solvent to VI. Suitable solvents include inert organic solvents, such as benzene, toluene, dichloromethane, chloroform, acetonitrile, dimethylformamide and the like. The reaction is conducted at a temperature of about 0° C. to about 150° C., and is generally complete within about 1 to about 10 hours. The product, Ia, is isolated using conventional procedures such as extraction, washing, filtration, concentration, recrystallization, chromatography and the like. Suitable metal cations include those of alkali metals such as sodium or potassium. If desired, VI may be prepared in situ by the combination of equivalent amounts of imidazole and sodium (or other alkali metal) in methanol. The methanol is removed by distillation and the sodium salt VI is used without further purification and/or isolation.

(b) Where n is 0 and Y is halogen:

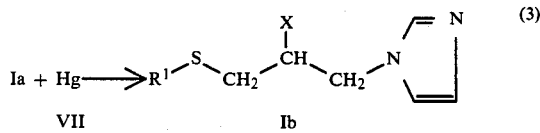

wherein $R^1$ is as previously defined in conjunction with Formula I, X is halogen and Hg is a halogenating agent.

Reaction (3) is conducted by combining Ia and VII in solvent. Although approximately equimolar amounts of Ia and VII may be used, it is preferred to use an excess of VII, on the order of about 1 to about 2 equivalents of VII per equivalent of Ia. The reaction is conducted at a temperature of about $-10°$ C. to about 50° C., preferably from about 0° C. to about 25° C., and is generally complete within about 1 to about 10 hours. Suitable halogenating agents, Hg, include thionyl chloride, phosphorus trichloride, phosphorus tribromide, phosphorus triiodide and the like. Although thionyl chloride is the preferred reagent for converting the hydroxy group to a chloro, other conventional reagents may be substituted for thionyl chloride. Suitable solvents include inert organic solvents such as methylene chloride, chloroform, toluene and the like.

(c) Where n is 0 and Y is —OCH$_2$R$^2$

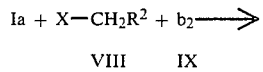

(4)

VIII     IX

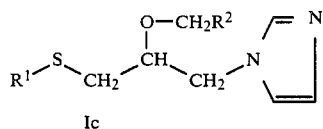

Ic wherein R$^1$ and R$^2$ are as defined in conjunction with Formula I, X is halogen and b$_2$ is a base.

Reaction (4) is conducted by adding VIII in solvent to a mixture of Ia and IX in solvent. Although approximately equimolar amounts of Ia, VIII and IX may be used, it is preferred to use an excess of VIII and IX in relation to Ia, on the order of about 1.1 to about 1.5 equivalents of VIII per equivalent of Ia, and about 1 to about 1.5 equivalents of IX per equivalent of Ia. Suitable bases, b$_2$, include strong bases such as sodium hydride, potassium tert-butoxide and the like. Suitable solvents include inert organic solvents such as dimethoxyethane, tetrahydrofuran, toluene and the like. The reaction is conducted at a temperature of from about −50° C. to about 50° C., preferably from about 0° C. to about 25° C. and is generally complete within about 1 to about 48 hours. The product Ic is isolated by conventional procedures such as extraction, washing, filtration, chromatography, trituration, and the like.

(d) Where n is 0 and Y is $$-\overset{O}{\underset{\|}{O}}\overset{}{\underset{}{C}}-R^3: Ia + Cl-\overset{O}{\underset{\|}{C}}-R^3 + b_3 \longrightarrow \quad (5)$$

X     XI

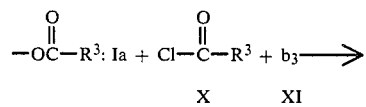

Id wherein R$^1$ and R$^3$ are as defined in conjunction with Formula I, and b$_3$ is a base.

Reaction (5) is conducted by combining Ia and X in the presense of XI. Although approximately equimolar amounts of Ia and X may be used it is preferred to use a slight excess of X, on the order of about 1 to about 1.5 equivalents X per equivalent Ia. Suitable bases b$_3$, include bases such as pyridine, triethylamine, sodium or potassium carbonate or bicarbonate, and the like. The reaction is conducted at a temperature of from about 0° C. to about 50° C., preferably from about 0° C. to about 25° C., and is generally complete within about 1 to about 48 hours. The product, Id, is isolated by conventional procedures such as extraction, washing, filtration, concentration, trituration, chromatography, and the like.

(e) Where n is 0 and Y is $$-\overset{O}{\underset{\|}{C}}NH-R^3 \text{ Ia} + R^3NCO \longrightarrow \quad (6)$$

XII

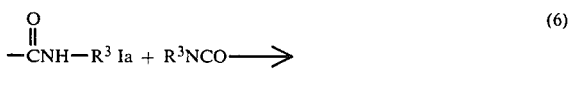

Ie wherein R$^1$ and R$^3$ are as previously defined in conjunction with Formula I.

Reaction (6) is conducted by combining Ia and XII in solvent. It is preferred to add an excess of XII relative to Ia, on the order of about 1 to about 1.5 equivalents XII per equivalent Ia. The reaction is conducted at a temperature of about 0° C. to about 100° C., preferably from about 30° C. to about 50° C., and is generally complete within about 1 to about 40 hours. Suitable solvents include inert organic solvents such as benzene, methylene chloride, toluene, and the like. It is preferred to add a small amount of catalyst such as dibutyl tin dilaurate. The product, Ie, is isolated by conventional procedures such as concentration, chromatography, trituration, recrystallization and the like.

(f) Where n is 1 or 2.

The compounds of Formula I where n is 1 or 2 may be conveniently prepared by oxidizing the corresponding sulfide according to the following reaction scheme:

(7)

$$R^1-S-CH_2-\underset{\underset{Y}{|}}{CH}-CH_2-N\diagup\hspace{-0.3em}=\hspace{-0.3em}\diagdown N + \text{COOOH-C}_6\text{H}_4\text{-Cl} \longrightarrow$$

If     XIII $$R^1-S(O)_m-CH_2-\underset{\underset{Y}{|}}{CH}-CH_2-N\diagup\hspace{-0.3em}=\hspace{-0.3em}\diagdown N$$

Ig wherein R$^1$ and Y are as previously defined in conjunction with Formula I and m is 1 or 2.

Reaction (7) is conducted by combining Ia and XIII in solvent. It is preferred to slowly add XIII in solvent to If in solvent. The reaction is conducted at a temperature of from about −10° C. to about 30° C., preferably from about 0° C. to about 25° C., and is generally complete within about 1 to about 10 hours. Suitable solvents include inert organic solvents such as methylene chloride, chloroform, toluene, methanol, and the like. The product Ig is isolated by conventional procedures such as extraction, washing, concentration, filtration, trituration and the like. It is well-established that peroxides, such as meta-chloroperoxybenoic acid (MCPBA) (XIII) and the like oxidize sulfide derivatives (such as If) to the corresponding sulfoxide or sulfone. To obtain the sulfinyl compound (m=1) corresponding to If, XIII is added in the ratio of approximately one equivalent XIII per equivalent If. Addition of XIII in the ratio of about two or more equivalents XIII per equivalent If yields the corresponding sulfone (m=2).

Alternatively, the sulfone compounds may be prepared directly according to the following reaction scheme:

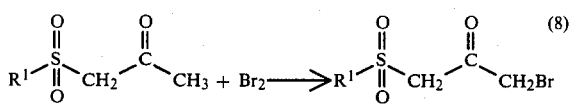 (8)

XIV    XV    XVI

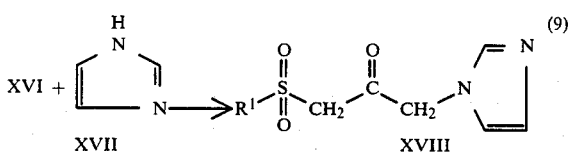 (9)

XVII    XVIII

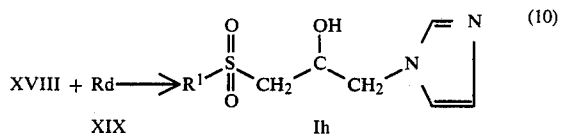 (10)

XIX    Ih wherein $R^1$ is defined in conjunction with Formula I and Rd is a reducing agent.

Reaction (8) is conducted by combining approximately equimolar amounts of XIV and XV in solvent. It is preferred to add XV in solvent to XIV in solvent. Suitable solvents include inert organic solvents such as carbon tetrachloride, methylene chloride, hexane and the like. The reaction is conducted at a temperature of from about 0° C. to about 100° C., preferably from about 20° C. to about 40° C. and is generally complete within about 1 to about 10 hours. The product, XVIII, is isolated by conventional procedures such as concentration, extraction filtration, trituration, recrystallization and the like.

Reaction (9) is conducted by combining XVI and XVII in solvent. An essentially equimolar amount of base is optionally added to the reaction mixture to scavenge the acid (HBr) generated. Suitable bases include bases which will form quaternary ammonium salts such as triethylamine, pyridine and the like. However, it is preferred to use an excess of XVII relative to XVI on the order of about 2 to about 5 equivalents XVII per equivalent XVI with the excess of base acting as the acid scavenger. Suitable solvents include inert organic solvents such as methylene chloride, acetonitrile, dimethylformamide, and the like. The reaction is conducted at a temperature of from about 0° C. to about 100° C., preferably from about 0° C. to about 30° C., and is generally complete within about 1 to about 24 hours. The product, XVIII, is isolated by conventional procedures such as concentration, extraction filtration, trituration, crystallization, and the like.

Reaction (10) is a conventional reduction of a carbonyl to a hydroxyl group. The reaction is conveniently conducted by adding reducing agent (Rd) XIX, to XVIII, on the order of about 1 equivalents to about 3 equivalents Rd (XIX) per equivalent XVIII. The reaction is conducted in the liquid phase employing solvents such as methanol, ethanol, isopropanol, water, tetrahydrofuran, and the like. Suitable reducing agents include, for instance, sodium borohydride, lithium aluminum hydride, borane, borane methyl sulfide, and the like. Preferably, convenience in handling and mildness in reducing activity, sodium borohydride is employed as the reducing agent. The reaction is conducted at a temperature of from about 0° C. to about 50° C., preferably from about 0° C. to about 30° C., and is generally complete within about 1 to about 5 hours. The product Ih is isolated by conventional procedures such as filtration, concentration, crystallization, chromatography, and the like.

Definitions

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group —$(CH_2)_m$— wherein m is an integer greater than zero. Typical alkylene groups include methylene, ethylene, propylene and the like.

The term "alkenyl" refers to unsaturated alkyl groups having a double bond (e.g., $CH_3CH=CHCH_2$—) and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro and bromo.

The term "alkoxy" refers to the group R'O— wherein R' is alkyl. The term "lower alkoxy" refers to alkoxy groups having from 1 to 6 carbon atoms; examples include methoxy, ethoxy, hexoxy, isopropoxy, and the like.

The term "carbalkoxy" refers to the group

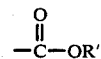

where R' is an alkyl group. The term "lower carbaloxy" refers to carbalkoxy groups where R' has a total of from 1 to 6 carbon atoms. Typical carbalkoxy groups include carbomethoxy, carbethoxy, and the like.

Some of the compounds of this invention are particularly effective in controlling plant fungal infections caused by organisms such as *Plasmopara viticola*. Some of the compounds of this invention are also useful for controlling leaf blights caused by organisms such as *Phytophthora infestans conidia, Alternaria solani conidia,* and *Septoria apii*. Some of the compounds of this invention are also useful for controlling fungal infections caused by *Uromyces phaseoli tipica, Erysiphe polygoni,* and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of

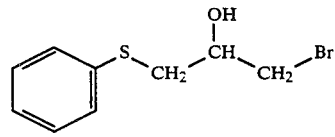

1-Bromo-3-phenylthio-propan-2-ol

Thiophenol, 11.0 g (0.10 mole), was added dropwise over a period of one hour, to a cold (0° C.) mixture of 13.69 g [8.5 ml (0.1 mole)] 1-bromo-2,3-epoxypropane (epibromohydrin), 1.5 ml [1.09 g (0.02 moles)] triethylamine and 1.5 ml methanol. The reaction mixture was then allowed to come to room temperature and was stirred at room temperature overnight. The solvent was removed in vacuo. The residue was dissolved in ether, washed several times with water and once with brine. The organic phase was dried over magnesium sulfate, filtered and concentrated to give 22.7 g of the above-identified product as an amber oil.

Example 2

Preparation of

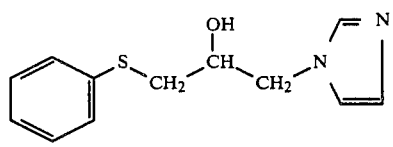

1-(1-Imidazolyl)-3-phenylthiopropan-2-ol

Sodium metal, 9.0 g (0.04 moles), was added to 150 ml methanol. The resulting mixture was stirred at room temperature for about 10 minutes, then 27.6 g (b 0.40 mole) imidazole in 50 ml methanol was added dropwise over about one-half hour. The mixture was heated; the methanol was removed by distillation (N₂ sweep) until the pot temperature reached 125° C. The heating element was turned off. Dimethylformamide 200 ml was added to the solid. The mixture was heated to 135° C. to remove residual methanol. 1-Bromo-3-phenylthiopropan-2-ol, 90 g (0.365 mole), in 100 ml benzene was added dropwise. The mixture was maintained at a temperature of about 125° C. during the addition which took about 1½ hours; during that time, benzene was removed by distillation at a rate about equal to the rate of addition. After the addition was complete, the mixture was stirred and benzene distilled. The heat was turned off and the mixture was stirred an additional 15 minutes. To the still hot solution, was added water and ice (about 250 ml). The mixture was cooled in an ice bath. The reaction mixture was extracted with ethyl acetate (three times with 300 ml). The combined ethyl acetate fractions were extracted once with water and five times with saturated brine.

The aqueous acidic phase was extracted once with ethyl ether/ethyl acetate (1:2), discarding the organic extracts, and then basified carefully with 50% sodium hydroxide to pH 9. The basic mixture was cooled in an ice-water bath, then extracted with ethyl acetate (twice 300 ml). The combined ethyl acetate phases were washed three times with semi-saturated brine, once with saturated brine, dried, filtered and concentrated to give 50.9 g of the above-identified product as a brown, viscous oil.

On standing, the oil solidified and was recrystallized from ethyl acetate and hexanes to yield a pale yellow solid, melting point 81°–83° C.

Elemental analysis for C₁₂H₁₄NOS: calculated %C 61.51, %H 6.02, and %N 11.95; found %C 59.54, %H 5.68, and %N 11.58.

Example 3a

Preparation of

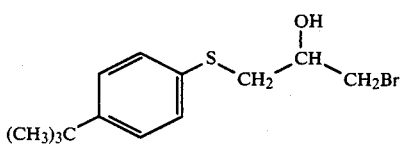

1-Bromo-3-(4'-tert-butylphenylthio)-propan-2-ol

To a stirred solution of 64.9 ml [103.67 g (0.758 mole)] 1-bromo-2,3-epoxypropane dissolved in 18 ml methanol/triethylamine (1:1) cooled to 5°–10° C. in a water-ice bath, 124.5 g (0.75 mole) p-tert-butylthiophenol was added dropwise. After the addition was complete (about 2¼ hours), the reaction mixture was allowed to come to room temperature and was allowed to stir at room temperature for about 2 hours. Volatiles were removed in vacuo to give 233.1 g of crude product as a viscous oil.

A 46.2 g aliquot of the above oil was dissolved in ethyl ether, washed with aqueous 5% sodium hydroxide (twice), with water (twice), and with a saturated brine solution. The organic phase was dried, filtered and remaining solvent was in vacuo to give 39.2 g of the above-identified product as a viscous, amber oil.

Elemental analysis for C₁₃H₁₉OSBr showed: calculated %C 51.49, and %H 6.31; found %C 55.39 and %H 6.74.

Example 3b

Preparation of

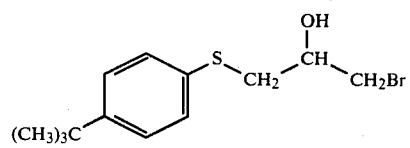

1-Bromo-3-(4'-tert-butylphenylthio)-propan-2-ol

To a stirred solution of 75.3 g [46.7 ml (0.55 mole)] 1-bromo-2,3-epoxypropane (epibromohydrin) in 14 ml 1:1 methanol/triethylamine cooled to 0°–5° C. in an ice-water bath, 83 g (0.5 mole) p-tert-butyl-thiophenol was added dropwise. After the addition was complete, the reaction mixture was allowed to come to room temperature and was stirred at room temperature for about 2 hours. The reaction mixture was dissolved in ethyl ether; washed with 1N sodium hydroxide, with 2N hydrochloric acid, with water until neutral and then with brine (twice). The organic phase was dried, filtered and concentrated to give 140.6 g of the above-identified product as an orange-red oil.

Example 4

Preparation of

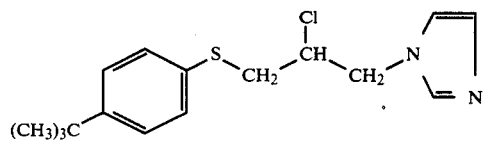

2-Chloro-1-(1-imidazolyl)-3-(4-tert-butylphenylthio)-propane

A mixture of 1-bromo-3-(4'-tert-butylphenylthio)-propan-2-ol, 5 g (0.0172 mole), in 10 ml methylene chloride was slowly added dropwise to 3.07 g [1.9 ml (0.0258 mole)] thionyl chloride cooled to 0° C. The reaction mixture was allowed to come to room temperature and was stirred for about five hours. A few drops of ethanol were added, then water was added. Sodium carbonate solution (5%) was added until the aqueous phase was basic (pH about 8). The phases were separated. The organic phase was washed with water until neutral, washed once with brine, dried, filtered, and concentrated to give an oil. The oil was placed on the high vacuum pump, yielding 5.2 g of the above-identified product as a brown oil.

Elemental analysis for C₁₆H₂₁Cl N₂S showed: calculated %C 63.04, %H 6.94, and %N 9.19; found %C 59.47, %H 6.95, and %N 8.55.

Example 5

Preparation of

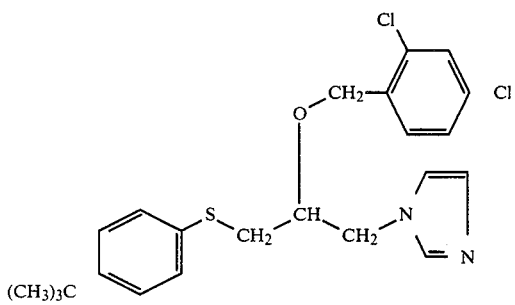

2-(2,4-Dichlorobenzyloxy)-1-(1-imidazolyl)-3-(4-tert-butylphenylthio)propane

A dry 250-ml round bottom flask equipped with stir bar, addition funnel and N₂ inlet was charged with dry dimethoxyethane (25 ml) and sodium hydride [60% (0.79 g, 0.0265 moles)]. The resulting slurry was cooled to −35° C. (with an external dry ice and acetone bath); then 1-(1-imidazolyl)-3-(4-tert-butylphenylthio)-propan-2-ol, 5.0 g (0.0172 moles), in 10 ml dry dimethoxyethane was added dropwise. After the addition was complete, the reaction mixture was allowed to warm to about −20° to −10° C. and was stirred at that temperature until no more H₂ evolution was apparent. The reaction mixture was then cooled to −20° C. and 3.7 g (0.0189 mole) 2,4-dichlorobenzyl chloride were added very slowly. After the addition was complete, the reaction mixture was allowed to come to room temperature and was allowed to stir overnight. The reaction mixture was poured into water and ice and then extracted with ethyl acetate (twice). The ethyl acetate extracts were combined and washed with water until neutral. The ethyl acetate phase was dried, filtered, and then concentrated to give an oil which was chromatographed to give 2.0 g of the above-identified product.

Elemental analysis for $C_{23}H_{26}Cl_2N_2OS$ showed: calculated %C 61.47, %H 5.83, and %N 6.23; found %C 62.84, %H 6.22, and %N 6.41.

Example 6

Preparation of

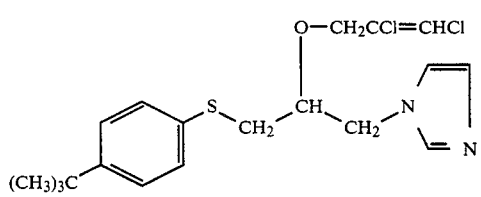

2-(2,3-Dichloroallyloxy)-1-(1-imidazolyl)-3-(4-tert-butylphenylthio)propane

A dry round bottom flask equipped with stir bar, addition funnel and N₂ inlet was charged with sodium hydride, [60%, 101 g (0.030 mole)] and dry dimethoxyethane (20 ml), then cooled (to about −25° C.) in a dry ice and carbon tetrachloride bath. Then, 1-(1-imidazolyl)-3-(4-tert-butylphenylthio)propan-2-ol, 5.0 g (0.172 mole), in dry dimethoxyethane (50 ml) was added dropwise. After the addition of the alcohol was complete and no more hydrogen gas evolved, 3.7 g (0.025 mole) 1,2,3-trichloropropene in dry dimethoxyethane (2 ml) was added dropwise. The reaction mixture was stirred at −25° C. for about one hour and then allowed to come to room temperature. After about two hours, the reaction was quenched with isopropyl alcohol (3 ml). The reaction mixture was poured into water (about 100 ml) and ice (50 ml). The mixture was extracted twice with ethyl acetate. The combined ethyl acetate extracts were washed with water (three times) and with brine, dried, filtered and concentrated to give 7.5 g of crude oil. HPLC of the crude product gave 2.0 g of the above-identified product as an amber oil.

Elemental analysis for $C_{19}H_{24}Cl_2N_2OS$ showed: calculated %C 57.14, %H 6.06, and %N 7.01; found %C 57.16, %H 6.46, and %N 6.92

Example 7

Preparation of

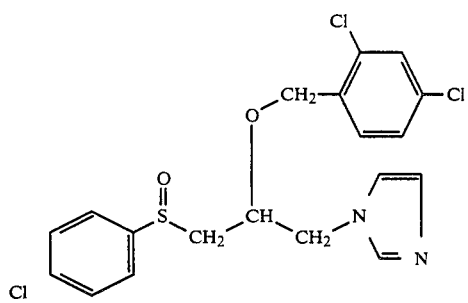

3-(4-Chlorophenylsulfinyl)-2-(2,4-dichlorobenzyloxy)-1-(1-imidazolyl)propane

To 6.1 g (0.0143 mole) 3-(4-chlorophenylthio)-2-(2,4-dichlorobenzyloxy)-1-(1-imidazolyl)propane in methylene chloride (25 ml) at 0° C., 2.8 g (0.0143 mole) 85% meta-chloroperoxybenzoic acid in methylene chloride (50 ml) were added dropwise over about 30 minutes. The reaction mixture was maintained at about 0° C. during the addition and for about 1½ to 2 hours after the addition. The reaction mixture was washed with a sodium bicarbonate solution (5%), with a bisulfite solution, dried, filtered, and concentrated to give 6.1 g of the above-identified product as a yellow oil.

Elemental analysis for $C_{19}H_{17}Cl_3N_2O_2S$ showed: calculated %C 51.42, %H 3.86, and %N 6.13; found %C 52.64, %H 4.49, and %N 6.16.

Example 8

Preparation of

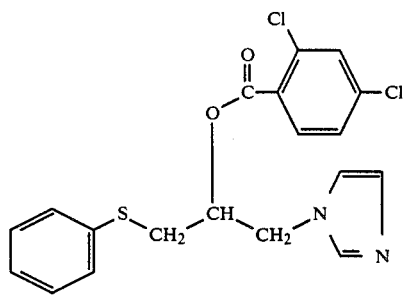

2-(2,4-Dichlorobenzoyloxy)-1-(1-imidazolyl)-3-phenylthiopropane

A mixture of 1-(1-imidazolyl)-3-phenylthiopropan-2-ol and 5 g (0.213 mole), in pyridine (15 ml) was cooled in an ice and water bath; then 4.9 g [3.3 ml (0.0235 mole)] 2,4-dichlorobenzoyl chloride was added dropwise. The reaction mixture was allowed to warm to room temperature and then stirred overnight. The resulting mixture was diluted with water and extracted with ethyl acetate. The organic phase was washed with a sodium bicarbonate solution, then several times with water and once with brine, dried, treated with activated charcoal, filtered and concentrated to give a brown gum (8.3 g).

Elemental analysis for $C_{19}H_{16}N_2O_2SCl_2$ showed: calculated %C 56.02, %H 3.96, and %N 6.88; found %C 51.93, %H 3.86, and %N 6.53.

Example 9

Preparation of

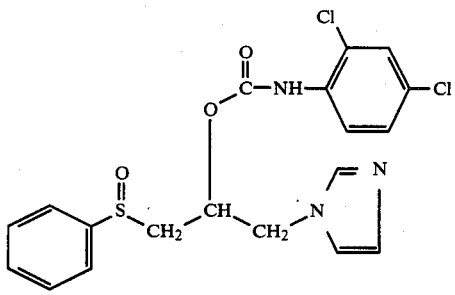

2-(N-2,4-Dichlorophenyl-carbamoyl)-1-(1-imidazolyl)-3-phenylthiopropane 1-(1-Imidazolyl)-3-phenylthiopropan-2-ol, 5.0 g (0.0214 mole), was added to a solution of 5.6 g (0.030 mole) 2,4-dichlorophenylisocyanate and dibutyltindilaurate (three drops) in 25 ml dry benzene. The reaction mixture was heated to about 50° C. for one-half hour, then stirred at room temperature overnight. The solvent was removed in vacuo to give 11.7 g of a viscous tan oil, which was then chromatographed on silica gel, eluting with 4% methanol in methylene chloride.

Elemental analysis for $C_{19}H_{17}Cl_2N_3O_2S$ showed: calculated %C 58.46, %H 4.39, and %N 10.77; found %C 65.16, %H 7.92, and %N 9.77.

Example 10

Preparation of

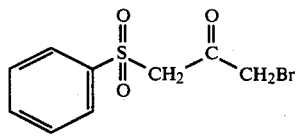

1-Bromo-3-phenylsulfonyl-propan-2-one

To a stirred suspension of 100.0 g (0.504 mole) phenylsulfonylacetone in 500 ml carbon tetrachloride, 80 g [25.7 ml (0.5 mole)] bromine dissolved in 75 g carbon tetrachloride were added dropwise. The reaction mixture was stirred at ambient temperature overnight. The reaction mixture was filtered, and the precipitate was washed with hexane to give 139.8 g of the above-identified product.

Example 11

Preparation of

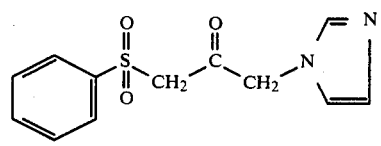

1-(1-Imidazolyl)-3-phenylsulfonylpropan-2-one

To a suspension of 50 g (0.180 mole) finely ground 1-bromo-3-phenylsulfonylpropan-2-one (the product of Example 10) in 125 ml methylene chloride cooled to about 0°-5° C., 36.8 g (0.54 mole) imidazole in 300 ml methylene chloride were added dropwise. The reaction mixture was maintained at 0°-5° C. for one hour, allowed to warm to room temperature and was stirred overnight. The methylene chloride was removed in vacuo at room temperature. The resulting oil was partitioned with 200 ml water and 200 ml ethyl acetate. The aqueous phase was extracted with ethyl acetate (four times 125 ml). The combined ethyl acetate extracts were treated with decolorizing charcoal, dried, filtered and concentrated. The precipitate which formed was triturated with methanol-isopropyl alcohol yielding 17.9 g of the above-identified product, as an off-white solid, melting point 137°-140° C.

Example 12

Preparation of

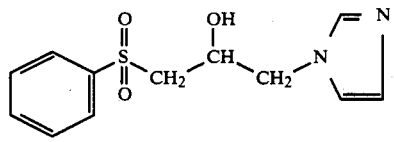

1-(1-Imidazolyl)-3-phenylsulfonyl-propan-2-ol

To a stirred mixture of 10 g (0.0377 mole) 1-(1-imidazolyl)-3-phenylsulfonylpropan-2-one (the product of Example 11) in 50 ml methanol cooled in an ice-water bath, 0.9 g (0.0237 mole) sodium borhydride, was added in 5 portions. The reaction mixture became viscous, and methanol (100 ml) was added. The reaction mixture was allowed to come to room temperature and to stir for about 1½ hours. The reaction mixture was cooled in an ice-water bath and the product removed by filtration. The precipiate was dried under vacuum to give 8.9 g of the above-identified product as an off-white solid, melting point 153°-156° C.

Example 13

Preparation of

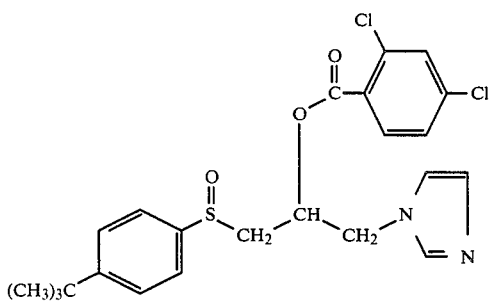

1-(1-Imidazolyl)-2-(N-2,4-dichlorophenylcarbamoyl)-3-(4-tert-butylphenylsulfinyl)propane To a stirred solution of 3.5 g (0.0073 mole) 1-(1-imidazolyl)-2-(N-2,4-dichlorophenylcarbamoyl)-3-(4-tert-butylphenylthio)propane in 25 ml methylene chloride cooled to 0° C., 1.44 g (0.0073 mole) of 85% meta-chloroperoxybenzoic acid in 50 ml methylene chloride was added dropwise. After the addition was complete, the reaction mixture was allowed to stir at 0° C. for about 1½ hours. The reaction mixture was washed once with 5% sodium bicarbonate, once with a saturated sodium bisulfite solution, three times with water and once with a saturated sodium chloride solution. The organic phase was then dried, filtered, and concentrated to give the above-identified product a solid, melting point of 70°-74° C.

Elemental analysis for $C_{23}H_{25}Cl_2N_3O_3S$ showed: calculated %C 55.87, %H 5.10, %N 8.50; found %C 54.92, %H 5.00, and %N 8.51.

Example 14

Preparation of

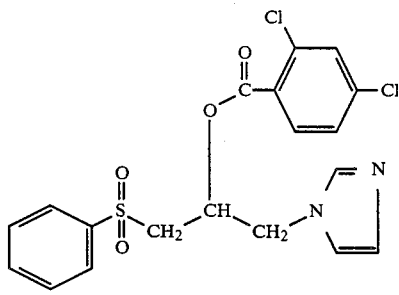

2-(2,4-Dichlorobenzoyloxy)-1-(1-imidazolyl)-3-phenylsulfonylpropane 1.7 ml (0.012 mole) 2,4-Dichlorobenzoyl chloride was added dropwise to 3.0 g (0.0113 mole) 2-(2,4-dichlorobenzoyloxy)-1-(1-imidazolyl)-3-phenylthiopropane and 8 ml pyridine coled to 0° C. After stirring at room temperature for about 10 minutes, the reaction mixture was homogeneous. The mixture was allowed to stand at room temperature overnight. The reaction mixture was diluted with water and ethyl acetate. The resulting solid was removed by filtration; recrystallization from water-acetonitrile gave the above-identified product, as a white solid, melting point 106°-109° C.

Elemental analysis for $C_{19}H_{16}Cl_2N_2O_4S$ showed: calculated %C 51.95, %H 3.67, and %N 6.38 found %C 50.16, %H 3.93, and %N 6.24.

Example A

Mycelial Inhibition

The compound was evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium monilofroma, Botrytis cinerea* and *Aspergillus niger*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99% control of the fungus ($ED_{99}$). The effectiveness of the compound for fungicidal activity is reported in Table II in terms of the percent of the $ED_{99}$ of the test compound of the $ED_{99}$ of the standard Difolatan ®.

Example B

Bean Powdery Mildew

The compound was tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

Example C

Tomato Late Blight

The compound was tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

Example D

Celery Late Blight

The Celery Late Blight test was conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

Example E

Tomato Early Blight

The compound was tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a non-ionic emulsifier. The sprayed plants were inoculated 1 day layer with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

Example F

Grape Downy Mildew

The compound was tested for the control of the Grape Downy Mildew organism, *Plasmopara viticola*. Seedlings of *Vitis vinifera* var. Emperor (7+ weeks old) were used as hosts. The plants were sprayed with a 250 ppm solution of the test compound in an acetone and water solution containing a small amount of non-ionic emulsifier. The treated plants were inoculated one day later by spraying them with a spore suspension of the organism. The treated plants were then held in a greenhouse at a temperature of about 68° F. to about 72° F. (relative humidify varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table II.

Example G

Bean Rust Eradicant

The compound was evaluated for their ability to eradicate Bean Rust caused by *Uromyces phaseoli tipica* on pinto beans.

Pinto bean plants variety Idaho 1-11, 16 (summer) or 19 (winter) days old were inoculated with a 50 ppm suspension of uredospores in water containing a small amount of non-ionic surfactant. The inoculated plants were placed in an environmental chamber immediately after inoculation and incubated 20 hours. Following the incubation period, the plants were removed from the chamber and placed in a greenhouse maintained at 66°–68° F. and 60–80% relative humidity. Two days after inoculation, the plants were treated by spraying with a 200 ppm solution of test compound in an acetone and water carrier formulation containing a small amount of non-ionic surfactant. One or two replicate pots (each containing two plants) were used for each compound. In addition, one or two replicate pots were sprayed with the same carrier formulation (without a test compound) as a control (hereinafter "untreated checks"). The plants were kept in the greenhouse until evaluated. The plants were evaluated for disease control when disease symptoms were well developed on the untreated checks, normally about 14 days after treatment. The percentage disease control (or eradication) provided by a test compound was based on the percent disease reduction relative to the untreated checks. The results are reported in Table II.

TABLE I

Compounds of the Formula:

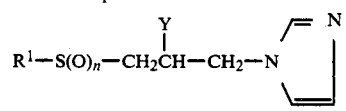

| Compound | n | R¹ | Y | Physical State | % C Calc. | % C Found | % H Calc. | % H Found | % N Calc. | % N Found |
|---|---|---|---|---|---|---|---|---|---|---|
| 1 33613 | 0 |  | —OH | Yellow oil | 61.51 | 59.54 | 6.02 | 5.68 | 11.95(?) | 11.58 |
| 2 33768 | 0 | 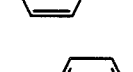 Cl— | —OH | Yellow-tan solid; mp 99–100 | 53.63 | 54.01 | 4.88 | 4.99 | 10.42 | 10.59 |
| 3 33906 | 0 |  (CH₃)₃C— | —OH | Yellow-brown oil | 66.14 | 66.84 | 7.64 | 7.94 | 9.65 | 9.69 |

TABLE I-continued
Compounds of the Formula:
$$R^1-S(O)_n-CH_2\overset{Y}{\underset{|}{CH}}-CH_2-N\diagup\hspace{-1em}\underset{\diagdown}{=}\hspace{-0.5em}N$$
| Compound | n | R[1] | Y | Physical State | %C Calc. | %C Found | %H Calc. | %H Found | %N Calc. | %N Found |
|---|---|---|---|---|---|---|---|---|---|---|
| 4 33505 | 2 |  | —OH | Off-white solid, mp 153–156 | 54.12 | 53.77 | 5.30 | 5.58 | 10.52 | 10.46 |
| 5 33614 | 2 | 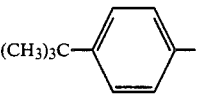 | —OH | Tan-solid, mp 155–158 | 59.59 | 58.60 | 6.88 | 7.07 | 8.69 | 8.28 |
| 6 34277 | 0 | 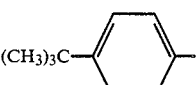 | —Cl | Brown oil | 63.04 | 59.47 | 6.94 | 6.95 | 9.19 | 8.55 |
| 7 34377 | 0 | 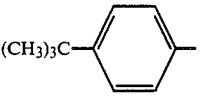 | —OCH₂CCl=CHCl | Amber oil | 57.14 | 57.16 | 6.06 | 6.46 | 7.01 | 6.92 |
| 8 33794 | 0 |  | 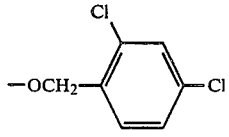 | Brown gum | 58.02 | 57.91 | 4.61 | 4.80 | 7.12 | 7.42 |
| 9 33898 | 0 | 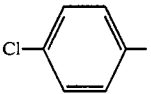 | 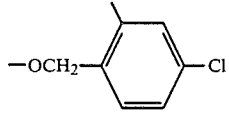 | Brown oil | 53.35 | 57.17 | 4.00 | 4.19 | 6.55 | 6.56 |
| 10 33970 | 0 | 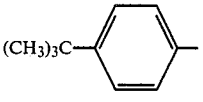 | 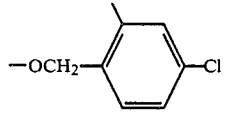 | Brown oil | 61.47 | 62.84 | 5.83 | 6.22 | 6.23 | 6.41 |
| 11 34043 | 1 |  | 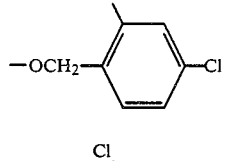 | Brown oil | 55.75 | 53.67 | 4.43 | 4.57 | 6.84 | 7.00 |
| 12 34044 | 1 | 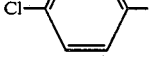 | 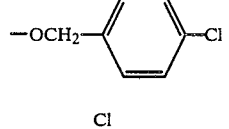 | Yellow oil | 51.42 | 52.64 | 3.86 | 4.49 | 6.13 | 6.16 |
| 13 34080 | 1 | 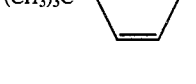 | 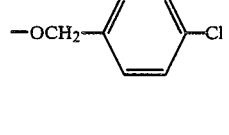 | Orange-yellow oil | 59.35 | 57.42 | 5.63 | 5.52 | 6.02 | 5.51 |

TABLE I-continued

Compounds of the Formula:

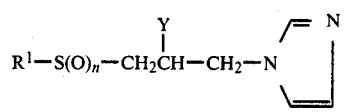

| Compound | n | R¹ | Y | Physical State | %C Calc. | %C Found | %H Calc. | %H Found | %N Calc. | %N Found |
|---|---|---|---|---|---|---|---|---|---|---|
| 14 33796 | 0 | phenyl | 2,4-dichlorobenzoyloxy | Brown gum | 56.02 | 53.65 | 3.96 | 3.81 | 6.88 | 6.62 |
| 15 33797 | 0 | 4-chlorophenyl | 2,4-dichlorobenzoyloxy | Yellow gum | 51.66 | 51.49 | 3.42 | 3.62 | 6.34 | 6.43 |
| 16 33907 | 0 | 4-tert-butylphenyl | 2,4-dichlorobenzoyloxy | Yellow oil | 59.61 | 59.98 | 5.22 | 5.43 | 6.04 | 6.41 |
| 17 33536 | 2 | phenyl | 2,4-dichlorobenzoyloxy | White solid mp 106–109 | 51.95 | 50.16 | 3.67 | 3.93 | 6.38 | 6.24 |
| 18 33767 | 2 | 4-tert-butylphenyl | 2,4-dichlorobenzoyloxy | Off-white mp 125–127 | 55.76 | 55.66 | 4.68 | 5.12 | 5.65 | 5.97 |
| 19 33795 | 0 | phenyl | 2,4-dichlorophenylcarbamoyloxy | Yellow gum | 48.46 | 65.16 | 4.39 | 7.92 | 10.77 | 9.77 |
| 20 33798 | 0 | 4-chlorophenyl | 2,4-dichlorophenylcarbamoyloxy | Orange-yellow gum | 49.96 | 46.27 | 3.53 | 3.55 | 9.20 | 8.42 |
| 21 33968 | 0 | 4-tert-butylphenyl | 2,4-dichlorophenylcarbamoyloxy | Yellow glass | 57.74 | 59.18 | 5.23 | 5.44 | 8.78 | 9.29 |
| 22 34079 | 1 | phenyl | 2,4-dichlorophenylcarbamoyloxy | Tan solid, mp 50–53 | 52.06 | 51.23 | 3.91 | 3.77 | 9.59 | 8.66 |

TABLE I-continued

Compounds of the Formula:

$$R^1-S(O)_n-CH_2CH(Y)-CH_2-N\underset{\diagup}{\diagdown}\begin{array}{c}N\\ \diagdown\end{array}$$

| Compound | n | R¹ | Y | Physical State | %C Calc. | %C Found | %H Calc. | %H Found | %N Calc. | %N Found |
|---|---|---|---|---|---|---|---|---|---|---|
| 23 34078 | 1 | (CH₃)₃C—C₆H₄— | —O—C(=O)—N(H)—(2-Cl,4-Cl-C₆H₃) | Tan solid, mp 70-74 | 55.87 | 54.92 | 5.10 | 5.00 | 8.50 | 8.51 |

TABLE II

Fungicidal Activity

| Compound | Mycelial Inhibition Pyth. | Rhiz. | Fus. | Botr. | Asp. | GDM | TLB | CLB | TEB | BR | BPM |
|---|---|---|---|---|---|---|---|---|---|---|---|
| 1 33613 | 0 | 0 | 0 | 0 | 0 | 0 | 0 | 0 | 11 | 0 | 0 |
| 2 33768 | 0 | 0 | 0 | 0 | 0 | 18 | 14 | 23 | 8 | 0 | 0 |
| 3 33906 | 0 | 0 | 0 | 0 | 0 | 65 | 0 | 39 | 51 | 14 | 11 |
| 4 33505 | 0 | 0 | 0 | 0 | 0 | 8 | 14 | 0 | 0 | 0 | 0 |
| 5 33614 | — | 0 | 0 | 0 | 0 | 0 | 0 | 39 | 23 | 0 | 8 |
| 6 34277 | 0 | 0 | 0 | 0 | 0 | 23 | 0 | 51 | 93 | 23 | 95 |
| 7 34377 | 0 | 24 | 0 | 0 | 0 | 6 | 35 | 88 | 95 | 0 | 86 |
| 8 33794 | 0 | 50 | 0 | 0 | 0 | 8 | 79 | 37 | 8 | 0 | 0 |
| 9 33898 | 0 | 140 | 0 | 0 | 0 | 74 | 14 | 81 | 68 | 0 | 0 |
| 10 33970 | 0 | 0 | 0 | 26 | 0 | 99 | 18 | 8 | 56 | 23 | 99 |
| 11 34043 | 0 | 0 | 0 | 0 | 0 | 44 | 29 | 63 | 88 | 0 | 0 |
| 12 34044 | 0 | 0 | 0 | 0 | 0 | 0 | 69 | 0 | 81 | 44 | 33 |
| 13 34080 | 0 | 0 | 0 | 0 | 0 | 0 | 98 | 21 | 23 | 0 | 76 |
| 14 33796 | 0 | 100 | 0 | 0 | 0 | 42 | 57 | 50 | 18 | 0 | 0 |
| 15 33797 | 0 | 50 | 0 | 0 | 0 | 29 | 86 | 23 | 42 | 0 | 0 |
| 16 33907 | 0 | 0 | 0 | 0 | 0 | 29 | 14 | 21 | 94 | 0 | 0 |
| 17 33536 | 0 | 0 | 0 | 0 | 0 | 11 | 23 | 0 | 84 | 0 | 0 |
| 18 33767 | 0 | 0 | 0 | 0 | 0 | 0 | 0 | 0 | 18 | 0 | 0 |
| 19 33795 | 0 | 87 | 0 | 0 | 0 | 54 | 92 | 50 | 29 | 0 | 0 |
| 20 33798 | 0 | 0 | 0 | 0 | 0 | 8 | 86 | 23 | 18 | 0 | 0 |
| 21 33968 | 0 | 0 | 0 | 0 | 0 | 0 | 18 | 8 | 21 | 0 | 0 |
| 22 34079 | 0 | 0 | 0 | 0 | 0 | 0 | 71 | 0 | 23 | 0 | 6 |
| 23 34078 | 0 | 0 | 0 | 0 | 0 | 0 | 98 | 0 | 63 | 0 | 100 |

Pyth. = *Pythium ultimum*
Rhiz. = *Rhizoctonia solari*
Fus. = *Fusarium monilofroma*
Botr. = *Botrytis cinerea*
Asp. = *Aspergillus niger*
GDM = Grape Downy Mildew
TLB = Tomato Late Blight
CLB = Celery Late Blight
TEB = Tomato Early Blight
BR = Bean Rust Eradicant
BPM = Bean Powdery Mildew

What is claimed is:

1. A compound of the formula:

$$R^1-S(O)_n-CH_2-CH(Y)-CH_2-N\underset{\diagup}{\diagdown}\begin{array}{c}N\\ \diagdown\end{array}$$

wherein n is 0, 1 or 2; R¹ is phenyl optionally substituted with 1 to 5 substituents independently selected from halogen, lower alkyl, lower alkoxy, nitro, cyano, lower carbalkoxy or amino optionally substituted with 1 or 2 lower alkyl groups; and Y is —OCH₂R² wherein R² is lower alkenyl optionally substituted with 1 to 5 halogen atoms or $$-O\overset{O}{\underset{\|}{C}}R^3$$

wherein R³ is phenyl optionally substituted with 1 to 5 substituents independently selected from halogen, lower alkoxy or nitro.

2. A compound according to claim 1 wherein n is 0.

3. A compound according to claim 1 wherein R¹ is unsubstituted or para-substituted with one substituent.

4. A compound according to claim 3 wherein said substituent is halogen or lower alkyl.

5. A compound according to claim 4 wherein said substituent is chloro or tert-butyl.

6. A compound according to claim 5 wherein R¹ is substituted with tert-butyl.

7. A compound according to claim 6 wherein $R^3$ is 2,4-dichlorophenyl.

8. A compound according to claim 7 wherein n is 0 and Y is

9. A compound according to claim 1 wherein $R^2$ is alkenyl optionally substituted with 1 to 5 halogen atoms.

10. A fungicidal composition which comprises a biologically inert carrier and a fungicidally effective amount of a compound of claim 1.

11. A fungicidal composition which comprises a biologically inert carrier and a fungicidally effective amount of a compound of claim 3.

12. A fungicidal composition which comprises a biologically inert carrier and a fungicidally effective amount of a compound of claim 8.

13. A fungicidal composition which comprises a biologically inert carrier and a fungicidally effective amount of a compound of claim 9.

14. A method of controlling fungi which comprises contacting said fungi or their growth environment with a fungicidally effective amount of a compound of claim 1.

15. A method of controlling fungi which comprises contacting said fungi or their growth environment with a fungicidally effective amount of a compound of claim 3.

16. A method of controlling fungi which comprises contacting said fungi or their growth environment with a fungicidally effective amount of a compound of claim 8.

17. A method of controlling fungi which comprises contacting said fungi or their growth environment with a fungicidally effective amount of a compound of claim 9.

* * * * *